United States Patent
Sarangapani et al.

[11] Patent Number: 6,129,928
[45] Date of Patent: Oct. 10, 2000

[54] BIOMIMETIC CALCIUM PHOSPHATE IMPLANT COATINGS AND METHODS FOR MAKING THE SAME

[75] Inventors: Shantha Sarangapani, Walpole, Mass.; Paul D. Calvert, Tucson, Ariz.

[73] Assignee: ICET, Inc., Norwood, Mass.

[21] Appl. No.: 09/148,724

[22] Filed: Sep. 4, 1998

Related U.S. Application Data

[60] Provisional application No. 60/058,105, Sep. 5, 1997.

[51] Int. Cl.[7] .................. A61F 2/28; A61K 33/42
[52] U.S. Cl. ............ 424/423; 423/323; 424/602; 427/2.26; 427/2.27; 435/176; 435/180; 435/181; 435/975; 623/16
[58] Field of Search ................. 427/2.25, 2.27, 427/2.29, 535, 419.8, 338, 327; 106/151.1, 151.2, 160.1; 423/158, 164, 323, 357, 358; 424/602, 605, 423; 435/176, 180, 181, 182, 975; 623/16

[56] References Cited

U.S. PATENT DOCUMENTS

| | | | |
|---|---|---|---|
| 3,908,680 | 9/1975 | Krezanoski | 134/27 |
| 4,366,183 | 12/1982 | Ghommidh et al. | 424/2.26 |
| 4,557,898 | 12/1985 | Greene et al. | 422/28 |
| 4,713,076 | 12/1987 | Draenert | 623/16 |
| 4,836,884 | 6/1989 | McAuslan | 427/2.24 |
| 4,871,384 | 10/1989 | Kasuga | 65/30.1 |
| 4,950,294 | 8/1990 | Hakamatsuka | 623/16 |
| 5,007,930 | 4/1991 | Dorman et al. | 623/16 |
| 5,010,009 | 4/1991 | Steele et al. | 427/2.24 |
| 5,030,474 | 7/1991 | Saita et al. | 427/2 |
| 5,079,093 | 1/1992 | Akashi et al. | 428/411.1 |
| 5,128,169 | 7/1992 | Saita et al. | 427/2 |
| 5,129,905 | 7/1992 | Constantz | 606/76 |
| 5,135,516 | 8/1992 | Sahatjian et al. | 604/265 |
| 5,219,926 | 6/1993 | Lindman et al. | 525/54.1 |
| 5,258,034 | 11/1993 | Furlong et al. | 623/23 |
| 5,272,012 | 12/1993 | Opolski | 428/423.1 |
| 5,292,362 | 3/1994 | Bass et al. | 427/2.24 |
| 5,446,090 | 8/1995 | Harris | 525/54.1 |
| 5,496,374 | 3/1996 | Blanchard | 623/16 |
| 5,508,046 | 4/1996 | Cosentino et al. | 424/616 |
| 5,599,587 | 2/1997 | Bowers | 427/322 |
| 5,652,016 | 7/1997 | Imura et al. | 427/212 |
| 5,667,753 | 9/1997 | Jacobs et al. | 422/29 |
| 5,674,450 | 10/1997 | Lin et al. | 422/29 |
| 5,698,265 | 12/1997 | Mucalo et al. | 427/333 |
| 5,733,868 | 3/1998 | Peterson et al. | 514/2 |
| 5,820,841 | 10/1998 | Chen et al. | 423/305 |
| 5,824,651 | 10/1998 | Nanci et al. | 427/2.26 |
| 5,868,749 | 2/1999 | Reed | 606/76 |

*Primary Examiner*—Diana Dudash
*Attorney, Agent, or Firm*—Hale and Dorr LLP

[57] ABSTRACT

This invention encompasses porous, nanocrystalline, biomimetic calcium phosphate coatings of the order of 2–30 microns that can be grown on metal implants. The chemical surface treatments and methods for making the calcium phosphate coatings are disclosed. Post treatment with dilute hydrogels such as phema reinforce the inorganic structure and enhance the mechanical strength of the coatings. Methods are also disclosed for adsorbing or covalently attaching growth factor proteins to derivatives of the hydrogel coated calcium phosphate coatings. Such hydrogel reinforced calcium phosphate coatings show equivalent bone tissue growth as the currently used implants and are easily resorbed. This property in combination with the immobilized growth factors is expected to enhance the process of osseointegration of the disclosed coatings.

87 Claims, 8 Drawing Sheets

BIOMIMETIC CALCIUM PHOSPHATE IMPLANT COATINGS AND METHODS FOR MAKING THE SAME

CROSS-REFERENCE TO RELATED APPLICATION

This application is related to provisional application No. 60/058,105 filed on Sep. 5, 1997 which is expressly incorporated herein by reference for all purposes.

This invention resulted from a Small Business Innovation Research contract from the U.S. National Institutes of Health, National Institute for Dental Research contract #1R43DE11756-01, 1996. The government may have certain rights in the invention.

FIELD OF THE INVENTION

The invention relates to calcium phosphate coatings on implants in orthopedic and dental applications.

BACKGROUND OF THE INVENTION

Metal implants are widely used both in orthopedic hip and knee surgeries and in dental surgery. Over 2 million orthopedic procedures and over 10 million dental implant procedures are performed in the United States every year. Implants fail because of poor osseointegration between the implant and the natural bone. Therefore, for the implants to function successfully, a direct chemical bond between the implant and the bone needs to form rapidly and needs to be retained over many years while the implant is loaded. Metal, however, does not form a direct chemical bond with bone. In order to promote osseointegration between the metal implant and bone, a layer of calcium phosphate ceramic material is coated onto the implants.

In current practice, calcium phosphate coatings are repeatedly applied using the mechanical and physical forces of plasma spraying. This method involves firing high temperature and high energy molten droplets of calcium phosphate at a high velocity onto the surface of the implant where they stick and freeze. Plasma sprayed calcium phosphate coatings have many disadvantages, though. Chief among these drawbacks is the inability to form thin coatings on the order of 25 microns or less. The process generally produces layers that are about 50 microns thick, remain on the implant for very long periods of time, and tend to delaminate under load, resulting in implant loosening. The slow resorption of calcium and the inability of bone cells to penetrate the thick, dense calcium phosphate layer cause the implant and calcium phosphate interface to weaken.

Accordingly, a need exists for a method of making a thinner biocompatible layer of calcium phosphate on metal implants for use in orthopedic and dental applications.

The present invention thus provides a low energy method of coating thin layers of biocompatible calcium phosphate onto metal implant surfaces. The novel method uses a biomimetic mechanism to produce thin, resorbable layers of calcium phosphate. These biomimetic calcium phosphate coatings may also be reinforced with hydrogel polymers to improve their mechanical strength. The invention also describes methods to immobilize bone inducing growth factors onto reactive hydrogel polymers that may accelerate the fixation of the implant to the bone. Other inventive features and advantages will become apparent from the following detailed description, examples, drawings and claims.

SUMMARY OF THE INVENTION

The present invention relates to new methods of pretreating the surface of an implant with chemicals to induce the formation biomimetic calcium phosphate coatings on such pretreated surfaces. The invention also discloses biomimetic calcium phosphate coatings. Briefly, the metal implant surface is roughened by grit blasting, oxidized to produce hydroxyl groups, and exposed to a high concentration of a nucleating agent. The hydroxyl groups on the surface of the metal react with the acidic functionalities of the nucleating agent to form a dense chemisorbed layer of nucleating agent on the surface of the implant. The implant surface, thus modified by the strong chemisorption of the nucleating agent, is subsequently exposed to a formulation containing calcium, phosphate, and a trace amount of the nucleating agent at a fixed pH. Within 24–48 hours of contact with the coating formulation, a uniform, thin coating of calcium phosphate appears on the implant. The thickness of the calcium phosphate can be regulated by controlling the time of exposure to the coating formulations. The examples described illustrate the preferred methodology for these coatings.

Another aspect of this invention is a formulation further comprising inert hydrogel polymers or hydrogel copolymers to reinforce the biomimetic calcium phosphate coatings. In addition, this invention discloses formulations further comprising certain reactive, derivatized hydrogel polymers and growth factor proteins. The reactive hydrogel polymers covalently bind to the amino acids of the growth factors and, hence, immobilize the growth factors onto the implant surface.

BRIEF DESCRIPTION OF THE DRAWINGS

FIG. 2. SEM views of the biomimetic hydroxyapatite coatings.

DETAILED DESCRIPTION OF THE INVENTION

Figure 1:
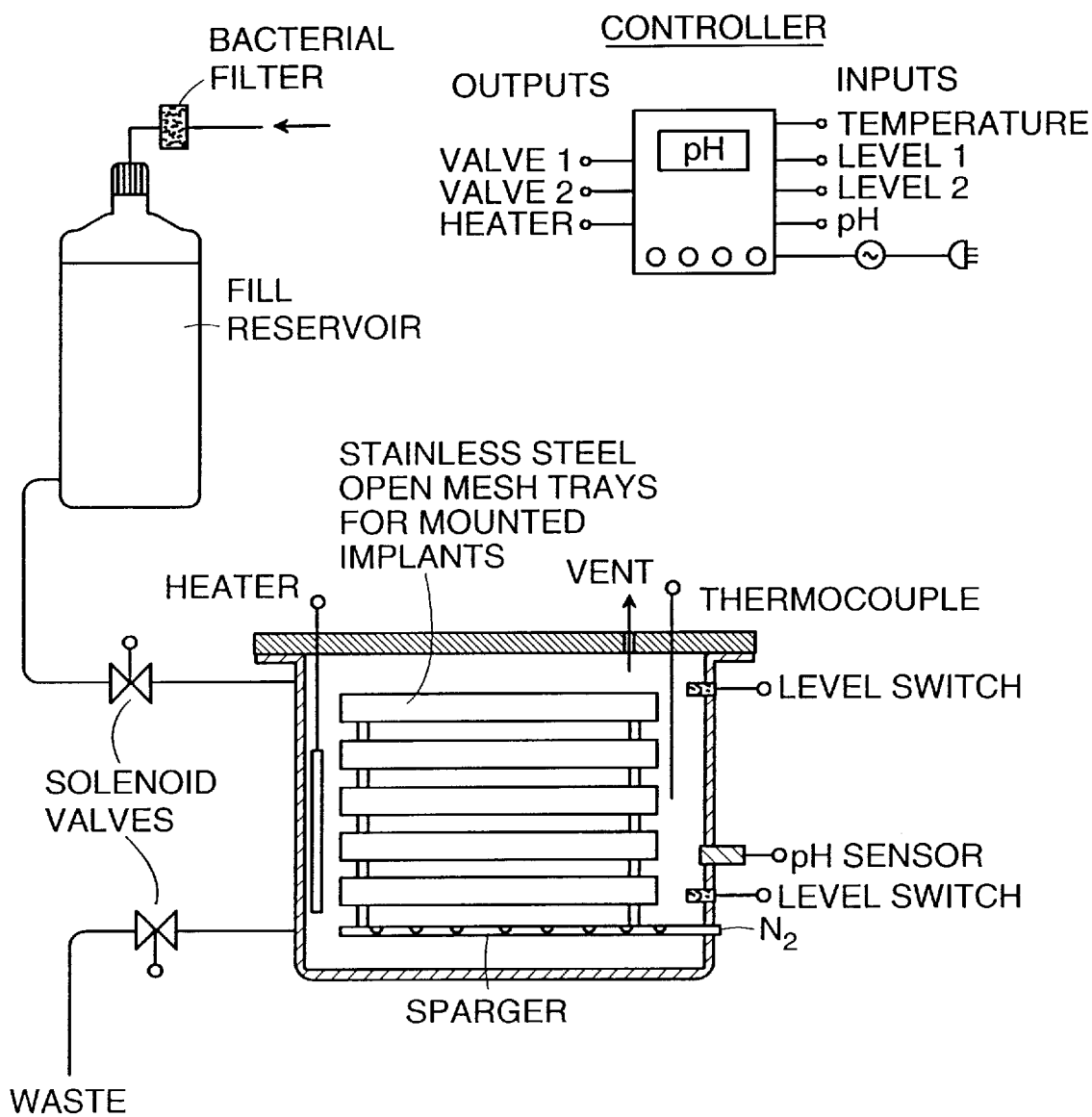
FIG. 1. A schematic of the batch reactor for preparing the biomimetic calcium phosphate coatings on implants.

Currently, plasma sprayed hydroxyapatite coatings are promoted as highly dense, resistant to resorption (dissolves slowly), highly crystalline (69%) and less than 5% porosity with pure 98.3%–99% hydroxyapatite content. The controversy over the importance of these parameters can be seen throughout the hydroxyapatite implant literature. For example, with respect to crystallinity, Bruijn et al. (*Cells Mater.* 3:115–127 (1993)) have recently shown that the crystallinity of the plasma sprayed hydroxyapatite coating is an important feature influencing cell response at the implant surface. According to Bruijn et al., the lower the crystallinity of a hydroxyapatite coating, the greater is the calcium resorption. This study reported that the implant surface formed a favorable interlocking between the bone forming cells and the coating. Maxian et al. (*Biomaterials Society Meeting*, 1993) have also shown that the greater surface activity of resorbable calcium phosphate coatings (with a high rate of dissolution) enhanced cell attachment and cell spreading. Particulate debris from highly crystalline bioactive materials is undesirable whereas chemical dissolution is desirable and may actually be a prerequisite for enhanced bone attachment and initiation of a carbonated hydroxyapatite layer. Active cellular resorption of hydroxyapatite coatings followed by phagocytosis of resorbed particles of multinucleated cells has been reported (Maxian et al., *J. Biomed. Mat. Res.* 27:717–728 (1993)), possibly altering the chemical interfacial bond between bone and implant in the long term.

Porous materials (pore size greater than 100 microns) allow bone cells to penetrate the coating and to grow in pores onto the metal implant, thus strengthening the union between the implant and the bone. (Langer and Vacanti, *Science* 260:920 (1996)). There is therefore a need to develop a resorbable, high area, porous calcium phosphate coatings with immobilized growth factors for bone fixation as an alternative to nonresorbable calcium phosphate coatings.

This invention discloses a solution-based method of rapidly producing thin (2–30 micron), porous, nanocrystalline (therefore high area) calcium phosphate crystallites on metal implants with strong interfacial chemical bonds between the metal and the initial calcium phosphate layers through a bridging nucleating agent. The oxidized implant surface is pretreated with a nucleating agent and is exposed to a coating solution comprising a trace amount of the nucleating agent and calcium and phosphate in a sufficient concentration to form calcium phosphate crystals.

The newly discovered method is comparable to a biomimetic mechanism that occurs in nature. Examples of natural biomimetic processes include the formation of shells, bones, and eggshells where layer organic macromolecules, such as proteins with anionic acidic functionalities, act as a template to control the nucleation and, hence, the growth of calcium containing minerals. Advantages of the novel biomimetic calcium phosphate coating include the fine control of crystallinity, density, surface roughness, and thinness.

Earlier efforts to coat implant materials by crystallization of hydroxyapatite from solution have had marginal success. These methods have encountered problems in that the hydroxyapatite coatings grow slowly, are very thin, adhere poorly, and are very soft. (Bunker et al., *Science* 264:48 (1994).) One possible answer to improve the speed of deposition and thickness of layers is to attach a nucleating agent to the metal surface. Accordingly, this invention has identified certain nucleating agents for inducing the biomimetic calcium phosphate coating onto the implant surface.

Strength and toughness are issues nor only for plasma spray calcium phosphate coatings, but also for biomimetic calcium phosphate coatings. Plasma sprayed coatings need to be strong to work successfully in vivo over time. The biomimetic coatings must also be tough in order to resist handling and the actual implant process. There is therefore a need to improve the strength of a calcium phosphate coating. Accordingly, the invention covers a method of reinforcing a calcium phosphate coating with a with hydrogel polymer or copolymerized hydrogel. The reinforcement enhances the mechanical strength of the coatings.

The hydrogel polymers form a strong, energy-absorbing bond with the calcium phosphate crystals. Depending upon the type of hydrogel polymer used, the polymer may be derivatized to allow simple adsorption or direct chemical attachment of growth factor proteins onto the surface of the implants.

The present invention covers methods for chemisorbing a nucleating agent onto the surface of a metal implant. The method preferably comprises the steps of oxidizing the implant by soaking the implant in a hot solution of hydrogen peroxide; and soaking the implant in a high concentration solution of the nucleating agent. The metal may be selected from tantalum, cobalt, chromium, titanium, a cobalt alloy, a chromium alloy, or a titanium alloy. The metal alloy is preferably a titanium alloy of 6% aluminum and 4% vanadium. The nucleating agent may be wherein the nucleating agent is a synthetic or natural compound or polymer that contains a phosphate, carboxyl, sulfonate, phosphonate, amino, or other acidic functionality. The nucleating agent is preferably phosphoserine, polyvinylphosphonic acid, polyvinylsulphonic acid, or phosphoric acid, most preferably phosphoserine.

The method, in another preferred embodiment, can include a roughening step prior to the oxidation step.

The invention also encompasses methods making a biomimetic calcium phosphate coating on the surface of a metal implant. Other preferred embodiments include a coating solution for preparing biomimetic calcium phosphate coating. The preferred coating solution comprises 3.5 mM calcium chloride, 2.6 mM potassium dihydrogen phosphate and 5–50 ppm phosphoserine, preferably 50 ppm phosphoserine, at pH 6.5. The coating solution may be used at 37–50° C., preferably at 50° C. Biomimetic coatings prepared with this solution and/or method have a thickness of 2–30 microns, preferably 5–15 microns, most preferably 15 microns.

Yet another preferred embodiment is a method of reinforcing the strength of a calcium phosphate coated metal implant with a hydrogel polymer. The method for reinforcing the calcium phosphate coatings comprises a heat treating step followed by a soaking step of the implant in a hydrogel polymer and drying the implant overnight in an oven. The hydrogel polymer is preferably hydroxyalkylacrylate or hydroxyalkylmethacrylate, more preferably polyhydroxyethylmethacrylate, polyhydroxypropylmethacrylate polyhydroxytetrafurfurylmethacrylate, polyhydroxyethylacrylate, polyhydroxypropylacrylate, polyhydroxytetrafurfurylacrylate. The most preferred hydrogel polymer is polyhydroxyethylmethacrylate.

Metal implants with other types of calcium phosphate coatings may be reinforced using the inventive methods. The other calcium phosphate coatings which fall within the scope of the invention include hydroxyapatite, tetracalcium phosphate, octacalcium phosphate, and mixed calcium phosphate phases. The calcium phosphate coatings may be plasma sprayed coatings or biomimetic coatings, such as the type described and claimed herein.

Another preferred method of reinforcing the strength of the calcium phosphate coatings on the metal implant is with a copolymerized hydrogel. The steps of this method include making a copolymer of a hydrogel by convention free radical polymerization in solvent; purifying the copolymerized hydrogel in a non-solvent; drying the copolymerized hydrogel as a powder; heating the calcium phosphate coated metal implant at 350° C.; soaking the metal implant in a solution of the copolymerized hydrogel; and drying the metal implant at 50–60° C. overnight.

A preferred method according to the instant invention is to make activated hydrogel polymers for coupling growth factor proteins, wherein the hydrogel reinforces calcium phosphate coatings on implants. The activated hydrogel polymers may, alternatively, be directly treated onto an implant without reinforcing a calcium phosphate coating. The activating method follows a first step of activating the hydrogel polymer by copolymerizing the hydrogel polymer with a space group molecule. The spacer group molecule has a protein reactive functional group. Next, a growth factor protein is coupled to the spacer group molecule at the protein reactive functional group. Preferentially, the spacer group molecule is a polyethyleneglycol acrylate or polyethyleneglycol methacrylate. The protein reactive functional group may be a n-hydroxy succinimide, tresylate, aldehyde, epoxide, pnp carbonate, cyanuric chloride, isocyanate, carbonyl imidazole, vinyl sulfone, maleimide, and dithioorthopyridine. Other protein reactive functional groups may include tresylate, aldehyde, epoxide, pnp carbonate, cyanuric chloride, isocyanate, carbonyl imidazole, vinyl sulfone, maleimide, dithioorthopyridine, cyanogen bromide, cyclic carbonate, chloroalkyl formate, cyclic azide, nitrophenylchloroformate, dialdehyde, isocyanate, diisocyanate. The most preferred protein reactive functional group is n-hydroxy succinimide. The spacer group molecule is most preferentially polyethyleneglycol acrylate n-hydroxy succinimide. According to this and other methods described below, the growth factor protein may be a transforming growth factor, an insulin-like growth factor, or a bone morphogenic growth factor. The growth factor protein most preferred is TGF-$\beta$.

Yet another inventive method is one for imbibing a growth factor protein into the reinforcing hydrogel polymer by soaking a calcium phosphate hydrogel reinforced coated implant in a dilute solution of growth factor.

Kits also fall within the claimed invention. These kits are useful for in situ coupling or absorption of growth factor proteins onto a calcium phosphate coated metal implant surface prior to implantation surgery. In a preferred kit, the kit may contain a calcium phosphate coated metal implant that is to be surgically implanted into a patient; a reactive hydrogel polymer dissolved in a suitable solvent; and a solution of growth factor proteins. A dentist or physician would soak the calcium phosphate coated metal implant first in the reactive hydrogel polymer solution and then in the growth factor solution. Other kits would include containers of a reactive hydrogel polymer that is first activated at a protein reactive functional group so as to covalently couple a growth factor protein.

EXAMPLE 1

Pretreatment Protocols

This example illustrates the pretreatment protocol to form a biomimetic hydroxyapatite coating on the surface of an implant material made of titanium alloy.

Implant Materials. An implant material made of a titanium alloy (6% aluminum, 4% vanadium) (President's Titanium, Hanson, Mass.) (ASTM F-136-92) was used to assess the different pretreatment protocols. The geometrical shapes for the coating trials were either cylindrical (4.8 mm diameter and 10 mm length) or flat surfaces. These implants included tensile buttons (1" diameter×¼" thickness), shear strength cylinders (¾" diameter) and rotating beam fatigue bars (½" diameter×4" wasp waist samples with hydroxyapatite coated on the curved region.) (APS Materials, Dayton, Ohio). Plasma spray coated implants made of the same titanium alloy were also studied (APS Materials).

Pretreatment: The standard pretreatment involved roughening the surface of the titanium implant, oxidizing the implant to produce hydroxyl groups, and then exposing the implant to a high concentration of a nucleating agent. The roughing step, however, may be omitted if the implant surface is porous, sintered, or mechanically prepared. Briefly, the roughening occurred by grit blasting each implant with medical grade aluminum oxide (SDT, Inc., Sharon, Mass.), followed by wash and rinse cycles (5 min. duration) in distilled water four times. The implant samples were then soaked in 1 M sodium hydroxide at 60–70° C. for about 15–20 min., rinsed well in distilled water, followed by a soak in 30% hydrogen peroxide for 1 hr. under conditions close to boiling. The samples were then treated with 5% phosphoserine (w/v) (Sigma-Aldrich, St. Louis, Mo.) in warm water for about 30 min. The phosphoserine nucleating agent becomes chemisorbed onto the oxidized titanium implant surface. After decanting the excess liquid, the treated implants were soaked in 0.5–1.0 M calcium chloride in a sodium hydroxide medium (pH 10) for 15 min. This soaking step was repeated and the samples washed and dried in an oven at 60–90° C. overnight. After these steps, an invisible layer of the calcium complexes of phosphoserine and calcium hydroxide has been deposited on the titanium implant surface.

Coating Process: The pretreated titanium implants were then mounted on polypropylene racks positioned in a closed glass reactor maintained at about 37–60° C. and filled with a coating solution of 3.5 mM calcium chloride, 2.6 mM potassium dihydrogen phosphate and 50 ppm of phosphoserine at a pH of 6.5. The solution was deaerated with nitrogen for 20–30 min. on a daily basis after sterile filtration after pH adjustment to 6.5. The solutions were changed every 24 hr. The coating solution was stirred continuously in the presence of the implants. The pH dropped one unit showing the formation of hydroxyapatite over each 24 hr. period. Usually within 24–48 hrs, a visible hydroxyapatite coating is seen on the titanium implant surface. At the end of 5 days, the biomimetic hydroxyapatite coating thickness ranges from 20–30 microns. The coating is quite adherent and the SEM shows evidence for crystal sizes averaging to about 100 nanometers long.

At the end of 5–7 days, the reactor was stopped and the coated implants rinsed with deionized water and dried in an oven at 60° C. overnight. At this point, a thin layer of a biomimetic hydroxyapatite coating has rapidly formed on the titanium implant surface.

Reinforcement Hydrogel Polymer: Some of the dried, biomimetic hydroxyapatite coated implants were reinforced with a hydrogel polymer by first heat treating the implant at 350° C. for 30 min. The heat treated implants were subsequently treated with the hydrogel polyhydroxyethylmethacrylate (phema) (Polysciences, Inc., Allentown, Pa.). The implants were soaked in a 2% phema (w/v) in 95% ethanol for about 15 min. and dried in an oven at about 50–60° C. overnight.

A scaled up version of the reactor for preparing the biomimetic hydroxyapatite coated implants shown in FIG. 1. The sterile filtered coating solution is fed in from the fill reservoir into the closed reactor tank containing the mounted implants. The solenoid valves automatically fill and empty the reactor tank. The sparger stirs the coating solution. Nitrogen is bubbled into the tank.

EXAMPLE 2

Mechanical Testing

The following mechanical tests were performed on biomimetic hydroxyapatite hydrogel reinforced implants and plasma sprayed hydroxyapatite implants following the FDA recommendations for testing the quality and performance of implants.

Shear Strength (ASTM F1658): Shear strength tests are made using ¾" diameter cylinders of biomimetic hydroxyapatite hydrogel reinforced test implants from Example 1. One end of a mating cylinder is glued using FM-1000 epoxy sheet glue to the hydroxyapatite coated end of the test implant. A fixture is used to hold the two cylinders in a tensile test machine. The two cylinders are pulled in opposite direction with the coating surface parallel to the pulling direction until failure.

Tensile Strength (ASTM F1147): Tensile strength tests are made using 1" diameter×¼" thick buttons of biomimetic hydroxyapatite hydrogel reinforced test implants from Example 1. Three tensile buttons are tested by gluing a 1" diameter test fixture to both the coated and back surface of the test button implant. The fixture is placed in the mating button of the same size to the coated surface using FM-1000 epoxy glue. Test fixtures are then placed in a tensile test machine and pulled perpendicular to the hydroxyapatite coated surface until failure.

Rotating Beam Fatigue (ASTM F1659): Rotating Beam Fatigue tests are made using ½" diameter×4" long wasp waist bars of biomimetic hydroxyapatite hydrogel reinforced test implants from Example 1. The samples are loaded with an applied force perpendicular to the sample axis and rotated under load for 10 million cycles without beam failure.

The results of these three mechanical tests are summarized in Table 1.

TABLE 1

| Test Type | Sample | Avg. Test Values, PSI |
| --- | --- | --- |
| Shear Strength | test implant | 4487 ± 65     N = 4 |
| Shear Strength | plasma sprayed implant | 8100 ± 1595     N = 5 |
| Tensile Strength | test implant | 9172 ± 540     N = 4 |
| Tensile Strength | plasma sprayed implant | 9280 ± 532     N = 5 |
| Rotating Beam | text implant | >10 million cycles passed |
| Rotating Beam | plasma sprayed implant | >10 million cycles passed |

Statistical analysis shows that the biomimetic hydroxyapatite hydrogel reinforced coating has a comparable tensile strength to the plasma sprayed hydroxyapatite coating and shows about 60% of the shear strength as the plasma sprayed hydroxyapatite coating. Both coatings display similar standards in the Rotating Beam Fatigue test.

EXAMPLE 3

Morphology Studies

Figure 2A:
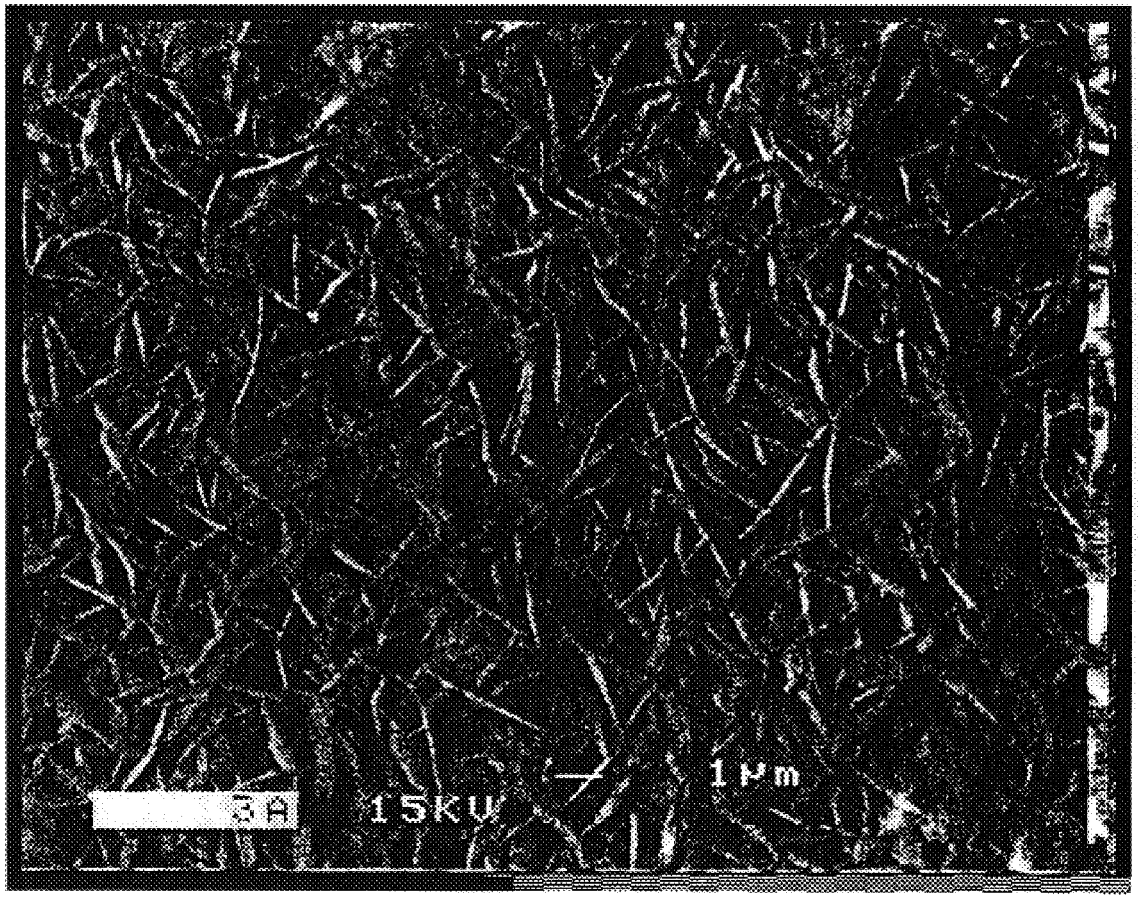
FIG. 2A is a 100 fold magnification.
Figure 2B:
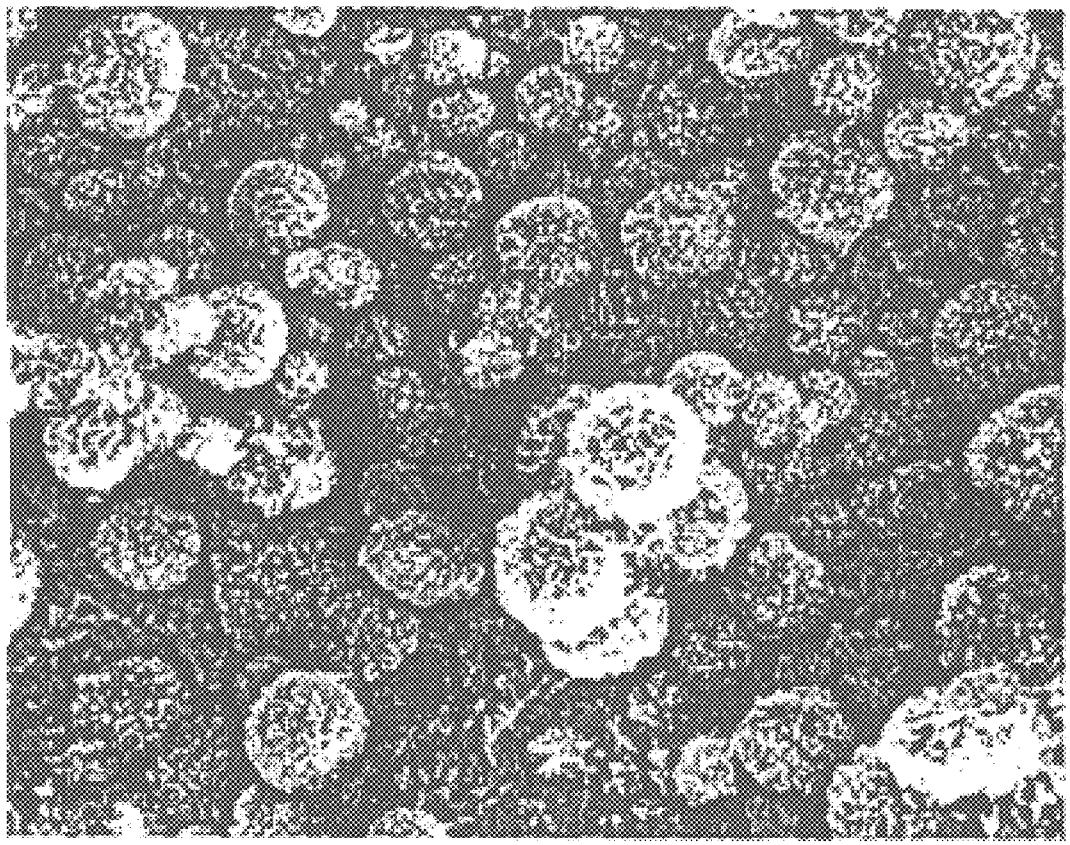
FIG. 2B is a 1000 fold magnification.

The morphology of the biomimetic hydroxyapatite hydrogel reinforced coating implants is shown in at SEM photos of their top surface in 100× and 1000× in FIGS. 2A and 2B, respectively.

X-ray diffraction and X-ray fluorescence studies are performed on test implants by Lambda Research (Cincinnati, Ohio). The X-ray fluorescence showed a Ca/P ratio of 1.5 instead of the expected 1.66 for hydroxyapatite. The reason for the high phosphorus may be the presence of adsorbed phosphoserine or trapped adsorbed calcium hydrogen phosphate thus lowering the Ca/P ratio. The coatings do not show signs of a significant amount of amorphous material. The X-ray peak widths are broadened, suggesting crystal size on the order of 25–30 nm by the Scherrer equation. Thus, the peak broadening is probably reflecting the actual thickness of the plate-like crystals, as opposed to some internal structure. Transmission electron microscopy is used to resolve this. The FTIR show clear evidence of hydroxyapatite and is comparable to that of pure hydroxyapatite.

EXAMPLE 4

In Vitro Bone Tissue Growth Studies

This example compares the ability of bone tissue to grow on the plasma sprayed hydroxyapatite coated implant surfaces and the biomimetic hydroxyapatite hydrogel reinforced implant surfaces.

Materials: Surgical grade titanium alloy (6% aluminum and 4% vanadium) flat sheets (1 mm thick) (President Titanium, Hanson Mass.) are punched to obtain flat circular implants. The resulting implants were 16 mm in diameter and could fit into standard 24 well tissue culture plates. The biomimetic hydroxyapatite hydrogel reinforced coated implants were prepared using the method described in Example 1. The coated implants were compared to plasma sprayed hydroxyapatite coated implants. The controls for the experiment included grit blasted titanium implants and tissue culture plates without implants.

Isolation and Culture of Bone Cells: Bone cells from post natal rat calvaria are collected by sequential collagenase digestion, and cultured to confluence in high glucose DMEM containing nonessential amino acids, 2 mM glutamine, 10% fetal calf serum, 1% penicillin/streptomycin B/amphotericin B, 50 µg/ml gentamicin solution and 1% HEPES buffer. All cultures are maintained at 37° C. in a humidified 5% $CO_2$ atmosphere, under standard sterile conditions. Media is changed every 48 hrs. for the first week and every 72 hrs. thereafter. Subculturing is done by trypsinization of cells following two washed with $Ca^{+2}$ and $Mg^{+2}$ free phosphate buffered saline (PBS) solution. Osteoblast phenotype is confirmed by alkaline phosphatase cytochemical staining (Sigma kit #86) and alkaline phosphatase enzyme activity. Cell counts are obtained with a hemocytometer.

Cell Culture Experiments: The flat circular implants are sterilized by ethylene oxide gas. Bone cells are seeded at a concentration of $5\times10^5$ cells per well in 1 ml of media on triplicate sets of the 5 different surfaces in 24 well tissue culture plates. Each experiment is repeated at three separate times using newly obtained calvarial cells. The average of each triplicate set from each of three experiments are used as n=1, 2, and 3 for statistical analyses. Two separate 24 well tissue culture plates are started at each time period: one for alkaline phosphatase activity (APA) and one for cell growth.

Alkaline Phosphatase Activity (APA): APA is determined by colorimetric assay with p-nitrophenylphosphate following removal of cells from the wells and implants. Briefly, at the indicated time period of 2, 7, and 14 days following culture, cell culture media is removed from each well and saved. Implants are rinsed 3 times in $Ca^{+2}$ and $Mg^{+2}$ free PBS and cells are detached from the implants and the culture plates after 10 min. of incubation with trypsin. The detached cells are removed from the wells in 1 ml PBS with 0.05% Triton X-100 and sonicated. To 100 µl of the cell solution in PBS/Triton is added 100 µl of substrate (1 mg/ml p-nitrophenylphosphate in 1 mM diethanolamine and 1 mM $MgCl_2$, pH9.8). The mixture is incubated at 37° C. for 60 min. The reaction is then stopped by the addition of 1 ml of 0.1 M NaOH. A standard curve is generated using known concentrations of p-nitrophenol. All samples and standards are measured on a spectrophotometer at 410 nm.

Cell Growth Determination: Cell growth was determined by an MTT (3-[4,5-dimethylthiazol-2-yl]-2,5-diphenyl tetrazolim bromide) colorimetric assay (Sigma kit #CDG-1) following incubation of attached cells. The MTT system is based on the principle that mitochondrial dehydrogenases of viable cells cleave the tetrazolium ring, yielding purple MTT formazan crystals which are insoluble in aqueous solutions. The crystals can be dissolved in isopropanol. An increase in cell number results in an increase in the amount of MTT formed and an increase in absorbency.

Statistical Analysis: For all test groups and parameters, the mean and standard error of the mean are calculated, and statistically significant ($p<0.05$) differences among the groups are determined using standard statistical techniques including multifactorial analysis of variance (ANOVA) and Student's t-Tests (Statgraphics Software, STSC, Inc., Rockville, Md.).

Figure 3:
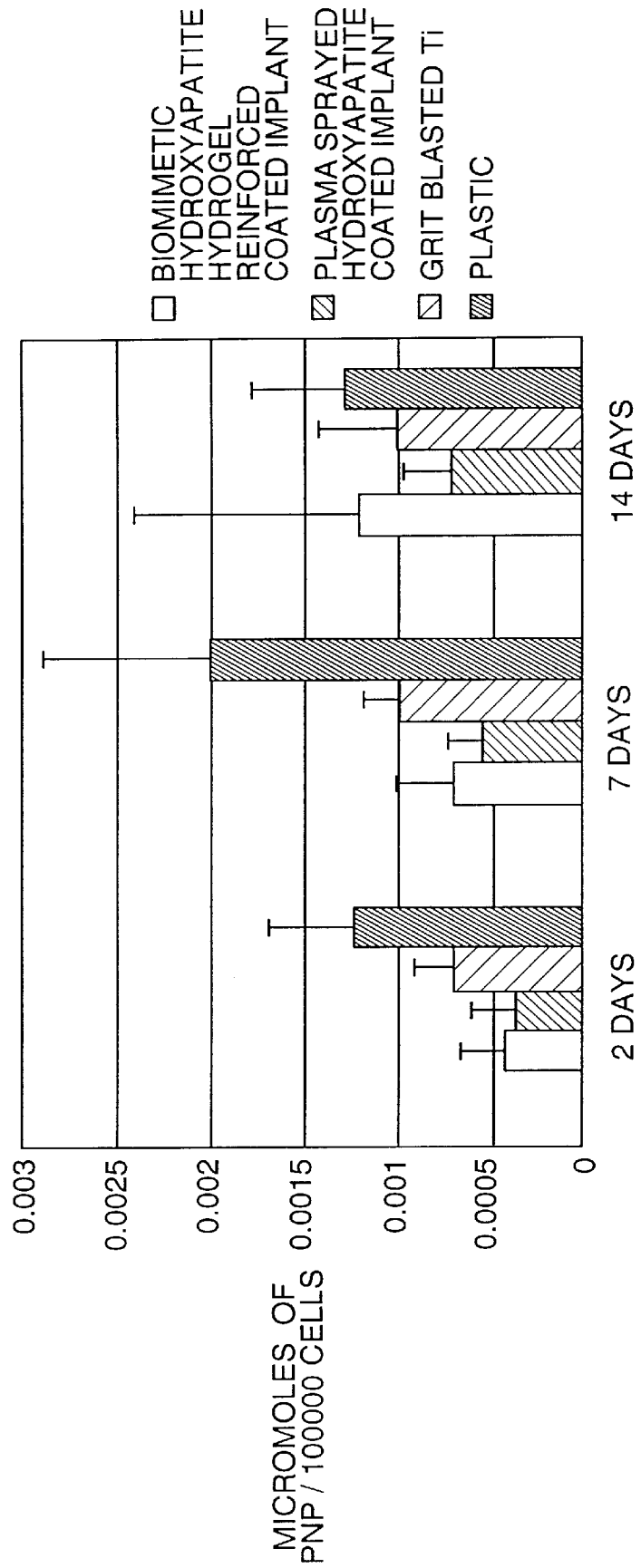
FIG. 3. Alkaline phosphotase activity of bone cells cultured in with different hydroxyapatite coatings.
Figure 4:
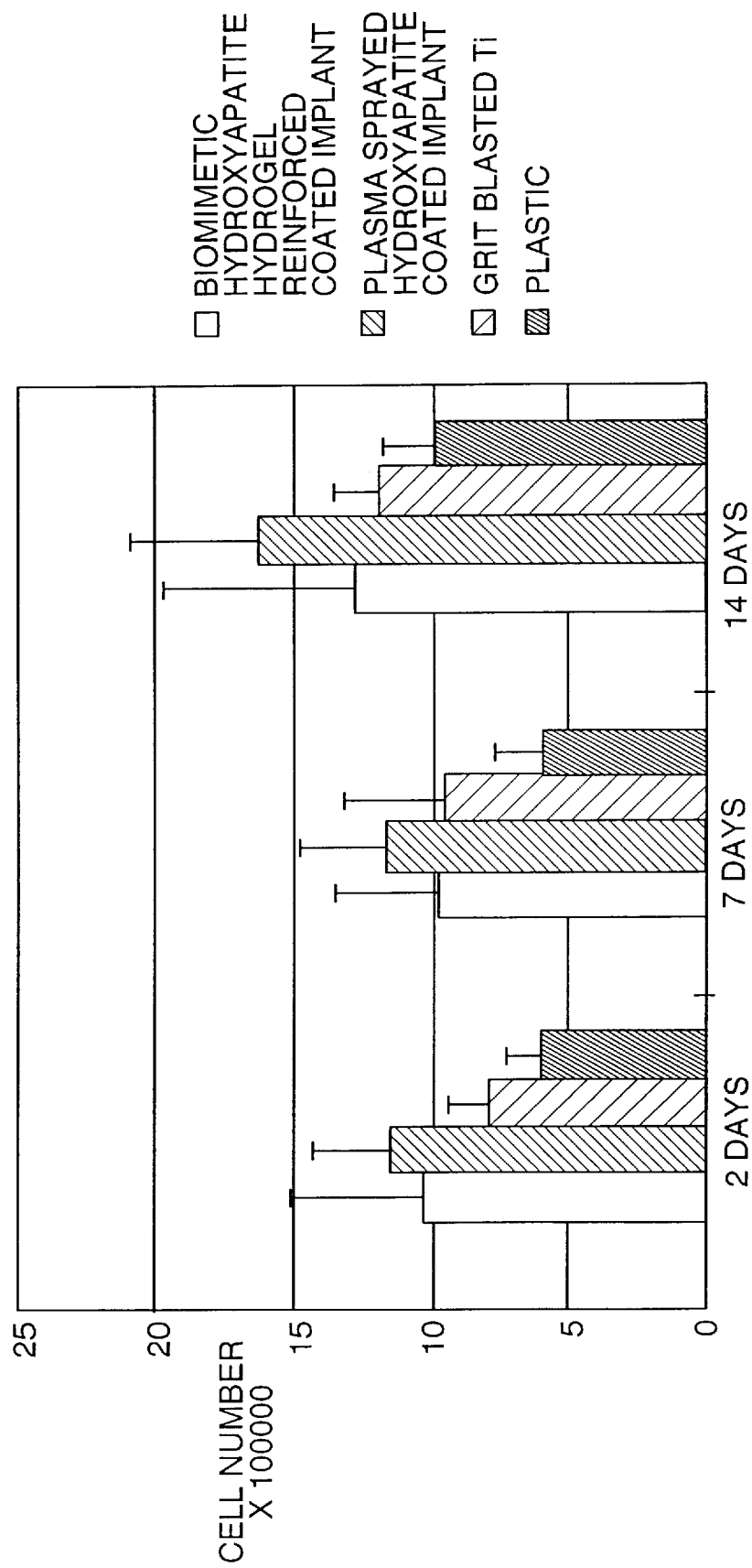
FIG. 4. Bone cell growth patterns are shown comparatively among different hydroxyapatite coatings.
Figure 5:
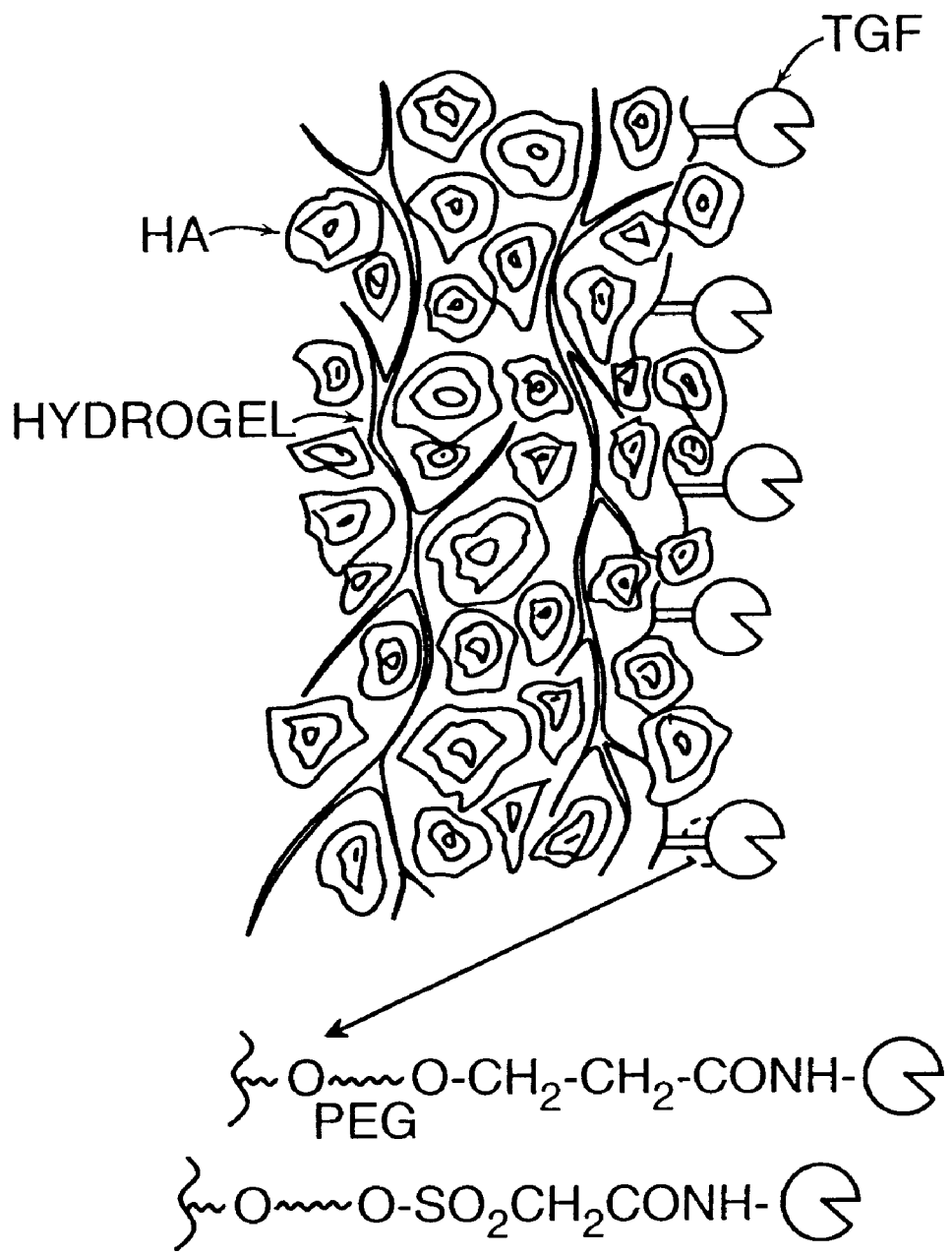
FIG. 5. Schematic for the covalent attachment of growth factors.

Results: The results of the APA assay are shown in FIG. 3 and the results of the cell growth determination are shown in FIG. 4.

It is shown that the biomimetic hydroxyapatite hydrogel reinforced coating was always equivalent to the plasma sprayed coating (no significant difference between the measured means ($p=0.52$) in terms of cell growth. The biomimetic hydroxyapatite hydrogel reinforced coating and the plasma sprayed hydroxyapatite coatings show similar cell growth than on grit blasted surface and all three were greater than plastic tissue culture well. The biomimetic hydroxyapatite hydrogel reinforced and plasma sprayed hydroxyapatite approach cell growth values for titanium by 14 days. (FIG. 4.)

In repeat blind study of comparison among the biomimetic coatings, it is confirmed that the biomimetic hydroxyapatite hydrogel reinforced coatings showed the highest cell growth over a period of 21 days.

The density of bone tissue grown on the biomimetic hydroxyapatite hydrogel reinforced coating and the conventional plasma sprayed coatings also have a comparable rating from the SEM micrographs. The results on the biomimetic hydroxyapatite hydrogel reinforced coated discs evaluated for bone tissue growth studies give a good spreading and proliferation of cells performing on par with the plasma sprayed hydroxyapatite coating showing that the reinforcing coating does not have any adverse effects. One can conclude that the biomimetic hydroxyapatite hydrogel reinforced coated surface has a very close similarity to the plasma sprayed hydroxyapatite in terms of biocompatibility and "bone friendly" nature.

EXAMPLE 5

Improvement of Mechanical Strength of the Biomimetic Coatings

This example provides for further improvements to the mechanical strength of the biomimetic hydroxyapatite hydrogel reinforced coatings. As evident above in Example 2, Table 1, the biomimetic coatings from this invention show about the same tensile strength as the plasma sprayed coated counter parts, but show only 60% of the shear strength of the plasma sprayed hydroxyapatite coatings. A system, described below, has been developed which imparts greater mechanical strength to the novel calcium phosphate coatings of the invention. This system may also be used with other calcium phosphate implant coatings, such as, for example, plasma spray coated hydroxyapatite.

Other copolymers will be developed from existing recognized biomedical acrylic polymers for improving mechanical strength. For example, copolymers of hydroxyethylmethacrylate (hema) can be used as a reinforcing hydrogel for hydroxyapatite coatings. Copolymerization hema with methylmethacrylate will provide greater strength and toughness in the water-swollen polymer. The extent of water-swelling can be modulated by addition of vinylpyrrolidone. Vinylphosphonate copolymerization can be used to provide improved bonding to the hydroxyapatite.

Copolymers of hema with methylmethacrylate and vinylpyrrolidone and copolymers of hema with vinyl phosphonic acid are prepared by conventional free radical polymerization in solvent (benzoyl peroxide catalyst at about 60° C.) and then purified by precipitation into non-solvent and dried as a powder.

This system can be optimized for composition and treatment conditions to provide good handling of the dry coatings, controlled swelling in body fluid to allow release of calcium and phosphate and a suitable surface energy for the coating to allow cell growth. These materials can be reinforced by impregnation into a calcium phosphate coated implant by a soaking process using an existing computer-controlled apparatus to provide reproducible coatings.

EXAMPLE 6

Preparation of Activated Phema Derivatives for Coupling Growth Factors

This example illustrates the method for treating biomimetic hydroxyapatite hydrogel reinforced coatings with reactive polymers. The reactive functionalities of the hydrogel are capable of chemically coupling with growth factor proteins.

Given that a polymer film is well bonded to the hydroxyapatite structure, it is of interest to bind bone growth factors to the hydrogel polymer reinforced coating to encourage bone ingrowth and maintenance. There are many possible chemical approaches, to couple the growth factors to the polymer, including: (1) modification of polymers or monomers for different protein coupling reactions with or without spacer groups; and (2) coupling of the growth factor protein to the polymer backbone using a coupling agent, as described in Example 7.

Modification with a spacer group: Polyethyleneglycol (PEG) (MW 3400) functionalized with acrylate at one end and n-hydroxy succinimide at the other end is available commercially (Shear Water Polymers, Huntsville, Ala., U.S.A.). This material, as well as other spacer groups such as PEG acrylates or PEG methacrylates (MW 400–20,000), can be incorporated into copolymers by conventional vinyl polymerization. (Yang et al, *J. Am. Chem. Soc.* 117:4843 (1995).)

The protocol will incorporate the protein coupling groups in the phema structure and thus prepare activated phema derivatives ready to couple the growth factors. The rationale for this approach is the ease and reproducibility of the active surface. Eventually this polymer could be sold as a part of a kit ready for coupling the growth factors. Short and long tethering molecule such as PEG may be used to evaluate the surface concentration of the growth factors.

EXAMPLE 7

Covalent Coupling Schemes

Figure 7:
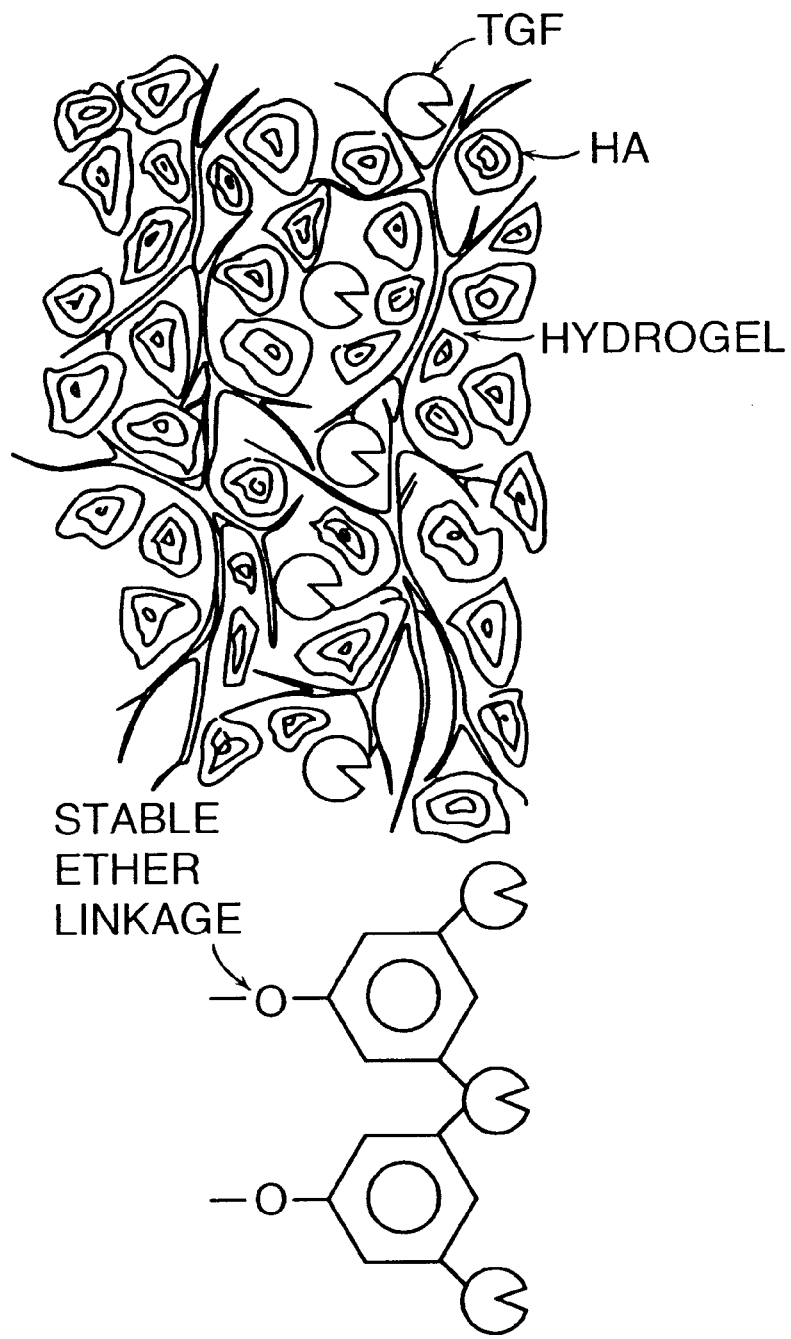
FIG. 7. Schematic of the adsorptive attachment of growth factors.

A covalent coupling reaction is shown schematically in FIG. 7. Several routes can be followed using reactive hydrogel polymers reinforced coatings to covalently couple a growth factor protein: (1) reaction of growth factors with a succinimide-functionalized polyethyleneglycolacrylate activated hydrogel prepared in Example 6; (2) isocyanate coupling of the growth factor protein to the isocyanate groups of a biocompatible polyurethane prepolymer; and (3) coupling of the growth factor protein using a coupling agent such as cyanuric chloride. These activations will result in a surface for an in situ coupling of the growth factor protein.

For example, growth factor such as TGF-$\beta$, (Becton-Dickinson, NJ at 37.4 mg/ml concentration is available) at a concentration ranging from 1.2 mg/ml–12 mg/ml) is exposed to the implants prepared according to Examples 1 and 6 above with the reactive surfaces (cylinders—10 mm length and 4.8 mm diameter). The medium of reaction is sodium acetate buffers in the pH of 5–7. The reaction time varies with the type of protein reactive group. Typically, the reaction times vary from 15 min. to 3 hrs. All reactions are carried out in Teflon coated containers under sterile conditions. The implants are then stored after adding 1 mg/ml bovine serum albumin in the buffer.

Another approach is the direct mixing of a medical grade polyurethane prepolymer such as Hypol 5000 or 2000 serirs (Hampshire Chemicals, NH) with microgram levels of the growth factors as a powder or in a nonaqueous medium. A typical coating formulation consists of Hypol or Perma™ prepolymer mixed with a growth factor such that the growth factor concentration is in the range of 10–500 parts per million. The mixture is diluted with acetone, THF or acetonitrile (10 g Hypol to 20–100 mL) and coated on to the calcium phosphate coated implant and moisture cured under ambient conditions.

Figure 6:
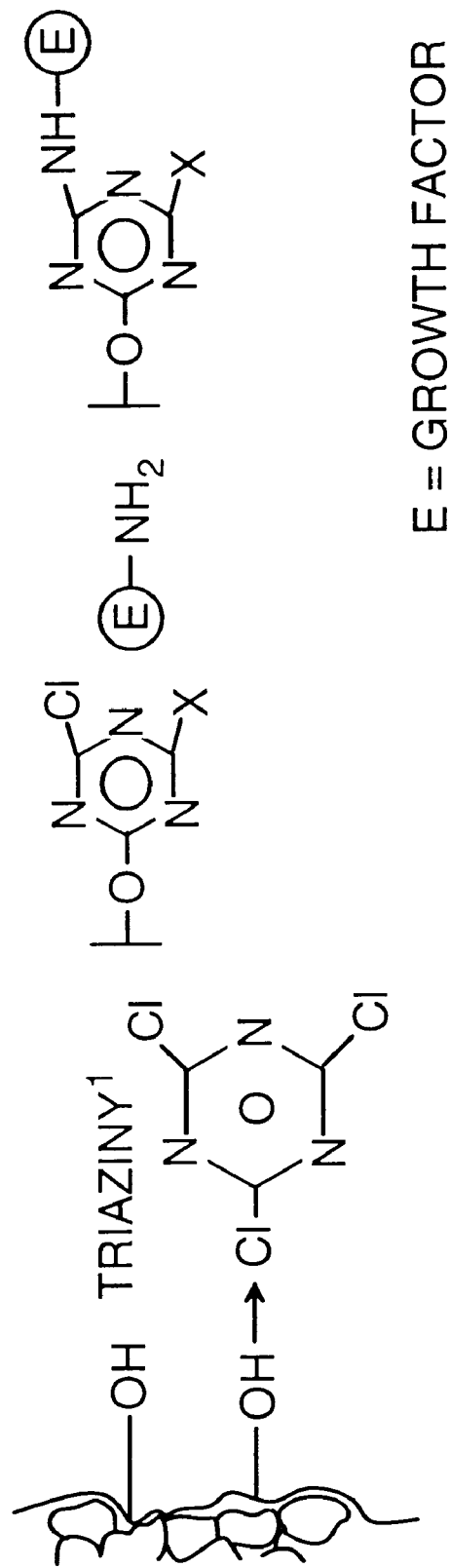
FIG. 6. Schematic of a coupling agent cyanuric chloride with a growth factor.

Yet another approach is to use the well-known coupling agent cyanuric chloride to covalently couple the biomimetic hydrogel reinforced coated surfaces and the growth factor proteins. (FIG. 6). The dry, hydrogel polymer impregnated surface of the calcium phosphate coating is exposed to trichloro triazine in a dry solvent, such as acetone which does not affect the phema. The extremely active first chlorine reacts instantaneously with the OH groups on the surface of the polymer. The second chlorine in aqueous solution at near neutral pH reacts with the protein amino groups and the third chlorine is deactivated by treatment with an amine.

EXAMPLE 8

Incorporation of the Bone Growth Factor by Imbibition or Adsorption into the Hydrogel Polymer Due to the high biocompatibility of the hydrogel polymer phema, several options exist for exploiting this material for loading growth factors. The permeabilities of phema and other hydrogels have been discussed in terms of dual mechanisms. The pore mechanism involves diffusion through aqueous channels of bulk like water: the solute-diffusion mechanism invokes transport via a domain composed of polymer, interfacial water and bound water. The observed changes in the flux and partition coefficients of solutes with different lipophilicities have been cited as evidence of the increasing importance of transport in the polymer phase for more lipophilic solutes. The determination of adsorption curves for the various growth factors will allow to precisely design and establish the concentration of the growth factor on the matrix surface as schematically represented in FIG. 7.

For example, the TGF-$\beta$ is diluted as in the previous example and 2 ml aliquots in Teflon coated sterile containers. Each implant is soaked in the aliquots for 1–4 hrs. Depending on the time of exposure, the TGF uptake by the hydrogel will vary. The ability of hydrogels to imbibe biomolecules is well known. (JMS-REV, Macromol. Chem. Phys. (32(1) (1–34) 1992.)

Having described a number of preferred embodiments of the present invention, and a number of specific examples thereof, it should be apparent that modifications can be made without departing from the scope of the present invention as defined by the appended claims.

What is claimed is:

1. A method of making a biomimetic calcium phosphate coating on the surface of a metal implant comprising the sequential steps of
   (1) chemisorbing a nucleating agent onto the surface of the metal implant comprising the steps of
      (a) oxidizing the implant by soaking the implant in a solution of hydrogen peroxide; and
      (b) soaking the implant in a solution comprising a nucleating agent;
   (2) decanting the excess solution comprising the nucleating solution;
   (3) soaking the metal implant in a solution comprising calcium chloride;
   (4) washing and drying the metal implant;
   (5) for a period of 5–7 days soaking the metal implant in a sterile, deaerated coating solution comprising calcium and phosphate in concentrations sufficient to form calcium phosphate crystals on the metal implant and a trace amount of the nucleating agent, wherein the solution is stirred and changed daily;
   (6) rinsing the metal implant; and
   (7) drying the metal implant.

2. The method according to claim 1, wherein the metal of the implant is selected from tantalum, cobalt, chromim, titanium, a cobalt alloy, a chromium alloy, or a titanium alloy.

3. The method according to claim 2, wherein the metal implant is titanium alloy.

4. The method according to claim 3, wherein the titanium alloy comprises 6% aluminum and 4% vanadium by weight.

5. The method according to claim 1, wherein the nucleating agent is a synthetic or natural compound or polymer that contains a phosphate, carboxyl, sulfonate, phosphonate, amino, or an acid.

6. The method according to claim 5, wherein the nucleating agent is phosphoserine, polyvinylphosphonic acid, polyvinylsulphonic acid, or phosphoric acid.

7. The method according to claim 6, wherein the nucleating agent is phosphoserine.

8. The method according to claim 1, wherein the nucleating agent solution of step 2 comprises 2–5% phosphoserine by weight.

9. The method according to claim 8, wherein the nucleating agent solution of step 2 comprises 5% phosphoserine by weight.

10. The method according to claim 1, wherein the surface of the metal implant is roughened by grit-blasting prior the oxidation step.

11. The method according to claim 1, wherein the calcium chloride solution in step 3 comprises 0.5–1.0 M calcium chloride and has a pH of 10.

12. The method according to claim 11, wherein the calcium chloride solution comprises 0.5 M calcium chloride.

13. The method according to claim 11, wherein the coating solution of step 5 comprises 3.5 mM calcium chloride, 2.6 mM potassium dihydrogen phosphate and 5–50 ppm phosphoserine at pH 6.5.

14. The method according to claim 13, wherein the coating solution of step 5 comprises 3.5 mM calcium chloride, 2.6 mM potassium dihydrogen phosphate and 50 ppm phosphoserine at pH 6.5.

15. The method according to claim 1, wherein the coating solution of step 5 is at 37–50° C.

16. The method according to claim 15, wherein the coating solution of step 5 is at 50° C.

17. The method according to claim 1, wherein the biomimetic calcium phosphate coating on the surface of a metal implant is 2–30 microns thick.

18. The method according to claim 17, wherein the biomimetic calcium phosphate coating on the surface of a metal implant is 5–15 microns thick.

19. The method according to claim 18, wherein the biomimetic calcium phosphate coating on the surface of a metal implant is 15 microns thick.

20. A method of reinforcing the strength of a calcium phosphate coated metal implant with a hydrogel polymer comprising the sequential steps of
  (1) heating the calcium phosphate coated metal implant at 350° C.,
  (2) soaking the metal implant in a solution comprising a hydrogel polymer; and
  (3) drying the implant at 50–60° C. overnight.

21. The method according to claim 20, wherein the hydrogel polymer is a hydroxyalkylacrylate or hydroxyalkylmethacrylate.

22. The method according to claim 21, wherein the hydrogel polymer is selected from the group consisting of polyhydroxyethylmethacrylate, polyhydroxypropylmethacrylate polyhydroxytetrafurfurylmethacrylate, polyhydroxyethylacrylate, polyhydroxypropylacrylate polyhydroxytetrafurfurylacrylate.

23. The method according to claim 22, wherein the hydrogel polymer is polyhydroxyethylmethacrylate.

24. The method according to claim 22, wherein the metal implant has a plasma sprayed hydroxyapatite coating.

25. The method according to claim 20, wherein the metal implant has a plasma sprayed calcium phosphate coating.

26. The method according to claim 20, wherein the metal implant has a plasma sprayed tetracalcium phosphate coating.

27. The method according to claim 20, wherein the metal implant has a plasma sprayed octacalcium phosphate coating.

28. The method according to claim 20, wherein the metal implant has a plasma sprayed calcium phosphate phase coating.

29. The method according to claim 20, wherein the metal implant has a biomimetic hydroxyapatite coating.

30. The method according to claim 20, wherein the metal implant has a biomimetic calcium phosphate coating prepared.

31. The method according to claim 20, wherein the metal implant has a biomimetic tetracalcium phosphate coating.

32. The method according to claim 20, wherein the metal implant has a biomimetic octacalcium phosphate coating.

33. The method according to claim 20, wherein the metal implant has a biomimetic calcium phosphate coating.

34. The method according to claim 20, wherein the metal of the implant is selected from tantalum, cobalt, chromium, titanium, a cobalt alloy, a chromium alloy, or a titanium alloy.

35. The method according to claim 34, wherein the metal implant is a titanium alloy.

36. The method according to claim 35, wherein the titanium alloy comprises 6% aluminum and 4% vanadium by weight.

37. The method of reinforcing the strength of a calcium phosphate coated metal implant with a copolymerized hydrogel comprising the sequential steps of:
  (1) making a copolymer of a hydrogel;
  (2) purifying the copolymerized hydrogel in a non-solvent;
  (3) drying the copolymerized hydrogel as a powder;
  (4) heating the calcium phosphate coated metal implant at 350° C.;
  (5) soaking the metal implant in a solution of the copolymerized hydrogel; and
  (6) drying the metal implant at 50–60° C. overnight.

38. The method according to claim 37, wherein the hydrogel polymer is a hydroxyalkylacrylate or hydroxyalkylmethacrylate.

39. The method according to claim 38, wherein the hydrogel polymer is selected from polyhydroxyethylmethacrylate, polyhydroxypropylmethacrylate polyhydroxytetrafurfurylmethacrylate, polyhydroxyethylacrylate, polyhydroxypropylacrylate polyhydroxytetrafurfurylacrylate.

40. The method according to claim 39, wherein the hydrogel polymer is polyhydroxyethylmethacrylate.

41. The method according to claim 37, wherein the hydrogel polymer is copolymerized with a vinyl monomer selected from acrylic acid, methacrylic acid, acrylonitrile, acrylamide, acrylate, methacrylate, butadiene, styrene, vinyl acetate, vinyl chloride, vinylidene chloride, and vinyl fluoride.

42. The method according to claim 37, wherein the copolymerized hydrogel is a copolymer of the hydrogel, methyl methacrylate, and polyvinylpyrrolidone or a copolymer of the hydrogel and polyvinylphosphonic acid.

43. The method according to claim 37, wherein the metal implant has a plasma sprayed hydroxyapatite coating.

44. The method according to claim 37, wherein the metal implant has a plasma sprayed calcium phosphate coating.

45. The method according to claim 37, wherein the metal implant has a plasma sprayed tetracalcium phosphate coating.

46. The method according to claim 37, wherein the metal implant has a plasma sprayed octacalcium phosphate coating.

47. The method according to claim 37, wherein the metal implant has a plasma sprayed calcium phosphate phase coating.

48. The method according to claim 37, wherein the metal implant has a biomimetic hydroxyapatite coating.

49. The method according to claim 37, wherein the metal implant has a biomimetic calcium phosphate coating.

50. The method according to claim 37, wherein the metal implant has a biomimetic tetracalcium phosphate coating.

51. The method according to claim 37, wherein the metal implant has a biomimetic octacalcium phosphate coating.

52. The method according to claim 37, wherein the metal implant has a biomimetic mixed calcium phosphate coating.

53. The method according to claim 37, wherein the metal of the implant is selected from tantalum, cobalt, chromium, titanium, a cobalt alloy, a chromium alloy, or a titanium alloy.

54. The method according to claim 53, wherein the metal implant is a titanium alloy.

55. The method according to claim 54, wherein the titanium alloy is a 6% aluminum and 4% vanadium titanium alloy.

56. A method of imbibing a growth factor into a reinforcing hydrogel polymer comprising the step of soaking a nanocrystalline calcium phosphate coated implant reinforced with a 2% (w/v) solution of the hydrogel polymer in a dilute solution of growth factor.

57. The method according to claim 56, wherein the growth factor protein is selected from a transforming growth factor, or a bone morphogenic protein.

58. The method according to claim 57, wherein the transforming growth factor protein is TGF-$\beta$.

59. A kit useful for in situ coupling or absorption of growth factor proteins onto a calcium phosphate coated metal implant surface prior to implantation surgery, the kit comprising one or more containers comprising:

(1) a nanocrystalline calcium phosphate coated metal implant that is to be surgically implanted into a patient;

(2) a 2% (w/v) solution of a reactive hydrogel polymer dissolved in a suitable solvent; and (3) a solution of growth factor proteins.

60. The kit according to claim 59, wherein the metal implant has a plasma sprayed hydroxyapatite coating.

61. The kit according to claim 59, wherein the metal implant has a plasma sprayed calcium phosphate coating.

62. The kit according to claim 59, wherein the metal implant has a plasma sprayed tetracalcium phosphate coating.

63. The kit according to claim 59, wherein the metal implant has a plasma sprayed octacalcium phosphate coating.

64. The kit according to claim 59, wherein the metal implant has a plasma sprayed calcium phosphate coating.

65. The kit according to claim 59, wherein the metal implant has a biomimetic hydroxyapatite coating.

66. The kit according to claim 59, wherein the metal implant has a biomimetic calcium phosphate coating.

67. The kit according to claim 59, wherein the metal implant has a biomimetic tetracalcium phosphate coating.

68. The kit according to claim 59, wherein the metal implant has a biomimetic octacalcium phosphate coating.

69. The kit according to claim 59, wherein the metal implant has a biomimetic calcium phosphate coating.

70. The kit according to claim 59, wherein the calcium phosphate coating further comprises, as reinforcement a hydrogel polymer.

71. The kit according to claim 59, wherein the calcium phosphate coating further comprises as reinforcement a copolymerized hydrogel.

72. The kit according to claim 59, wherein the growth factor protein is selected from a transforming growth factor or a bone morphogenic growth factor.

73. The kit according to claim 72, wherein the growth factor protein is TGF-$\beta$.

74. The kit according to claim 59, wherein the hydrogel polymer is a hydroxyalkylacrylate or hydroxyalkylmethacrylate.

75. The kit according to claim 74, wherein the hydrogel polymer is selected from polyhydroxyethylmethacrylate, polyhydroxypropylmethacrylate, polyhydroxytetrahydrofurfurylmethacrylate, polyhydroxyethylacrylate, polyhydroxypropylacrylate, and polyhydroxytetrahydrofurfurylacrylate.

76. A method of making activated hydrogel polymers for coupling growth factor proteins, wherein the hydrogel reinforces calcium phosphate coatings on implants, comprising the steps of (1) activating the hydrogel polymer by copolymerizing the hydrogel polymer with a spacer group molecule, wherein the spacer group molecule has a protein reactive functional group, (2) coupling a growth factor protein to the spacer group molecule at the protein reactive functional group.

77. The method according to claim 76, wherein the spacer group molecule is a polyethyleneglycol acrylate or polyethyleneglycol methacrylate.

78. The method according to claim 76, wherein the protein reactive functional group is selected from the group consisting of n-hydroxy succinimide, tresylate, aldehyde, epoxide, cyanuric chloride, isocyanate, carbonyl imidazole, vinyl sulfone, maleimide, and dithioorthopyridine.

79. The method according to claim 76, wherein the spacer group molecule is polyethyleneglycol acrylate n-hydroxy succinimide.

80. The method according to claim 76, wherein the growth factor protein is selected from a transforming growth factor or a bone morphogenic growth factor.

81. The method according to claim 80, wherein the growth factor protein is TGF-$\beta$.

82. The method according to claim 76, wherein the hydrogel polymer is a hydroxyalkylacrylate or hydroxyalkylmethacrylate.

83. The method according to claim 82, wherein the hydrogel polymer is selected from polyhydroxyethylmethacrylate, polyhydroxypropylmethacrylate, polyhydroxytetrahydrofurfurylmethacrylate, polyhydroxyethylacrylate, polyhydroxypropylacrylate, and polyhydroxytetrahydrofurfurylacrylate.

84. The method according to claim 56, wherein the implant is coated with calcium phosphate crystals having a size between 25 and 100 nanometers long.

85. The method according to claim 84, wherein the crystals have a size between 25 and 30 nanometers long.

86. The method according to claim 59, wherein the implant is coated with calcium phosphate crystals having a size between 25 and 100 nanometers long.

87. The method according to claim 86, wherein the crystals have a size between 25 and 30 nanometers long.

* * * * *